US012631588B2

(12) United States Patent
Kato et al.

(10) Patent No.: US 12,631,588 B2
(45) Date of Patent: May 19, 2026

(54) CARBON DIOXIDE SENSOR

(71) Applicants: MITSUI KINZOKU COMPANY, LIMITED, Tokyo (JP); KYUSHU UNIVERSITY, NATIONAL UNIVERSITY CORPORATION, Fukuoka (JP)

(72) Inventors: Kohei Kato, Ageo (JP); Shingo Ide, Ageo (JP); Kengo Shimanoe, Fukuoka (JP); Ken Watanabe, Fukuoka (JP); Koichi Suematsu, Fukuoka (JP); Nan Ma, Fukuoka (JP)

(73) Assignees: MITSUI KINZOKU COMPANY, LIMITED (JP); KYUSHU UNIVERSITY, NATIONAL UNIVERSITY CORPORATION (JP)

( * ) Notice: Subject to any disclaimer, the term of this patent is extended or adjusted under 35 U.S.C. 154(b) by 544 days.

(21) Appl. No.: 17/779,281

(22) PCT Filed: Dec. 17, 2020

(86) PCT No.: PCT/JP2020/047231
§ 371 (c)(1),
(2) Date: May 24, 2022

(87) PCT Pub. No.: WO2021/132029
PCT Pub. Date: Jul. 1, 2021

(65) Prior Publication Data
US 2022/0390411 A1 Dec. 8, 2022

(30) Foreign Application Priority Data
Dec. 25, 2019 (JP) ................................. 2019-235316

(51) Int. Cl.
*G01N 27/407* (2006.01)
*G01N 33/00* (2006.01)

(52) U.S. Cl.
CPC ..... *G01N 27/4075* (2013.01); *G01N 27/4073* (2013.01); *G01N 27/4074* (2013.01); *G01N 33/004* (2013.01)

(58) Field of Classification Search
CPC .............. G01N 27/4073–4076; G01N 33/004
See application file for complete search history.

(56) References Cited

U.S. PATENT DOCUMENTS

| | | | | |
|---|---|---|---|---|
| 2004/0158410 A1 * | 8/2004 | Ono | | G01N 33/004 |
| | | | | 702/24 |
| 2005/0109617 A1 | 5/2005 | Ono et al. | | |
| 2010/0282618 A1 * | 11/2010 | Wang | | G01N 33/0054 |
| | | | | 205/780.5 |
| 2013/0224628 A1 * | 8/2013 | Moon | | H01M 4/8657 |
| | | | | 429/479 |
| 2018/0183068 A1 * | 6/2018 | Ide | | H01M 8/12 |

FOREIGN PATENT DOCUMENTS

| | | | | | |
|---|---|---|---|---|---|
| DE | 19503783 A1 * | 8/1996 | ......... | G01N 27/4074 |
| JP | 2004-239832 A | 8/2004 | | |
| JP | 2005-172630 A | 6/2005 | | |
| JP | 2008-224637 A | 9/2008 | | |
| JP | 2009008575 A * | 1/2009 | | |
| WO | 2008-267845 A | 11/2008 | | |
| WO | 2019-203219 A1 | 10/2019 | | |

OTHER PUBLICATIONS

Miura, Noria et al., Sensors and Actuator B 24-25 (1995) 260-265, "Solid-state potentiometric CO2 sensors using anion conductor and metal carbonate" (6 pages).
International Search Report (English and Japanese) issued in PCT/JP2020/047231, mailed Mar. 9, 2021; ISA/JP (6 pages).

* cited by examiner

Primary Examiner — James Lin
Assistant Examiner — Vivian A Tran
(74) Attorney, Agent, or Firm — Harness, Dickey & Pierce, P.L.C.

(57) ABSTRACT

A carbon dioxide sensor includes: a solid electrolyte layer that is anion conductive; a reference electrode disposed on one surface of the solid electrolyte layer; and a detection electrode disposed on the other surface of the solid electrolyte layer. The detection electrode is made of a mixture containing: (a) one or more metals selected from the group consisting of Au, Ag, Pt, Pd, Rh, Ru, Os, and Ir; (b) a cation conductive carbonate; and (c) an oxide containing Li and at least one of Ce and Sm. The solid electrolyte layer is preferably oxide ion conductive, and the cation conductive carbonate is preferably lithium ion conductive.

16 Claims, No Drawings

CARBON DIOXIDE SENSOR

CROSS REFERENCE TO RELATED APPLICATIONS

This application is a U.S. National Phase application under 35 U.S.C. 371 of International Application No. PCT/JP2020/047231, filed on Dec. 17, 2020, which claims priority to Japanese Patent Application No. 2019-235316, filed on Dec. 25, 2019. The entire disclosures of the above applications are expressly incorporated by reference herein.

BACKGROUND

Technical Field

The present invention relates to a sensor that is preferably used to detect or quantify carbon dioxide gas in an atmosphere.

Related Art

Oxide ion conductors are materials that are attracting attention as functional ceramics applicable to various electrochemical elements, such as solid-state electrolytes for batteries such as solid-state electrolyte fuel cells, ion batteries, and air batteries, as well as sensors and separation membranes. Sensors and Actuators B24-25 (1995) 260-265 proposes a carbon dioxide sensor as an electrochemical element in which an oxide ion conductor is utilized. The carbon dioxide sensor includes: an oxide ion-conductive solid-state electrolyte that is made of magnesium-stabilized zirconia; a lithium ion-conductive carbonate auxiliary phase that is made of lithium carbonate; and an ion bridge that is made of $Li_2ZrO_3$ and provided therebetween. $Li_2ZrO_3$ for the ion bridge is formed by a reaction between magnesium-stabilized zirconia and lithium carbonate. The ion bridge is formed for the purpose of electrochemically connecting the oxide ion-conductive solid-state electrolyte and the lithium ion-conductive carbonate auxiliary phase.

JP 2008-267845A also discloses a carbon dioxide sensor. The sensor includes a solid-state electrolyte that is made of yttrium-stabilized zirconia, and a reference electrode and a detection electrode made of lithium carbonate both on the solid-state electrolyte. A $Li_2ZrO_3$ crystal phase as a conductive layer for both ions is provided between the solid-state electrolyte and the detection electrode. The conductive layer for both ions is formed using a gas phase method.

The carbon dioxide sensors disclosed in JP 2008-267845A and Sensors and Actuators B24-25 (1995) 260-265 operate at a high temperature of 600° C. or more, and thus there is a need for a carbon dioxide sensor that operates at a lower temperature.

Also, the carbon dioxide sensors disclosed in JP 2008-267845A vary in the electromotive force depending on the thickness of the conductive layer for both ions, and it is therefore not easy to perform accurate measurement. Furthermore, since the conductive layer for both ions is formed using a gas phase method, it takes a long time to form the conductive layer.

Likewise, the carbon dioxide sensors disclosed in Sensors and Actuators B24-25 (1995) 260-265 as well vary in the electromotive force depending on the thickness of the ion bridge, and since the ion bridge is formed by a reaction, it is not easy to obtain a constant thickness.

Accordingly, an object of the present invention is an improvement in a carbon dioxide sensor, and more specifically, is to provide a carbon dioxide sensor that can operate at a temperature lower than the operating temperatures of conventional carbon dioxide sensors and has less variability in the electromotive force among the sensors.

SUMMARY

The present invention achieves the object described above by providing a carbon dioxide sensor including: a solid electrolyte layer that is anion conductive; a reference electrode disposed on one surface of the solid electrolyte layer; and a detection electrode disposed on the other surface of the solid electrolyte layer, wherein the detection electrode is made of a mixture containing:

one or more metals selected from the group consisting of Au, Ag, Pt, Pd, Rh, Ru, Os, and Ir;

a cation conductive carbonate; and an oxide containing Li and at least one of Ce and Sm.

DETAILED DESCRIPTION

Hereinafter, the present invention will be described by way of preferred embodiments thereof. The carbon dioxide sensor according to the present invention is preferably used to detect or quantify carbon dioxide gas in an atmosphere. The carbon dioxide sensor according to the present invention includes a solid electrolyte layer. The solid electrolyte layer is anion conductive. The anion depends on the material of the solid electrolyte layer, and examples thereof include oxide ions and fluoride ions. The shape of the solid electrolyte layer is not particularly limited, and the solid electrolyte layer may have any of various types of shapes. In view of improving the measurement accuracy of the carbon dioxide sensor, the solid electrolyte layer preferably has a plate shape.

A reference electrode is disposed on one surface of the solid electrolyte layer, and a detection electrode is disposed on the other surface of the solid electrolyte layer. That is, the detection electrode is disposed on the surface opposite to the surface on which the reference electrode is disposed. The reference electrode is an electrode that comes into contact with an atmosphere having a known carbon dioxide concentration. On the other hand, the detection electrode is an electrode that comes into contact with an atmosphere as an object of measurement.

The positional relationship between the solid electrolyte layer, the reference electrode, and the detection electrode is not particularly limited. For example, a reference electrode and a detection electrode that have the same size as that of the solid electrolyte layer when viewed in a plan view may be disposed. Alternatively, a reference electrode and a detection electrode that are smaller than the solid electrolyte layer when viewed in a plan view may be disposed. In this case, the reference electrode and the detection electrode may be disposed in a positional relationship in which they entirely or partially overlap each other when viewed in a plan view, or in a positional relationship in which they do not overlap each other at all when viewed in a plan view.

The detection electrode is preferably made of a mixture of a plurality of specific materials. The mixture contains the following three types of materials (a) to (c):

(a) one or more metals selected from the group consisting of Au, Ag, Pt, Pd, Rh, Ru, Os, and Ir;

(b) a cation conductive carbonate; and (c) an oxide containing Li and at least one of Ce and Sm (hereinafter also referred to as "lithium-containing oxide").

Hereinafter, these materials will be described.

The metal (a) is used mainly for the purpose of imparting electron conductivity to the detection electrode. Also, the metal (a) may be used to impart catalysis for facilitating electrochemical reactions to the detection electrode. From this viewpoint, the metal (a) is one or more metals selected from the group consisting of Au, Ag, Pt, Pd, Rh, Ru, Os, and Ir, and the metal (a) is preferably one or more metals selected from the group consisting of Au, Ag, and Pt. It is also possible to use electron conductive metal oxides such as zinc oxide and indium oxide.

The metal or metal oxide (a) is generally used in the form of particles. The particle size is preferably 0.01 μm or more and 10 μm or less, more preferably 0.05 μm or more and 5 μm or less, and even more preferably 0.1 μm or more and 3 μm or less, in terms of the 50th percentile of the volume-weighted particle size distribution, $D_{50}$, as determined by a laser diffraction scattering. The particle shape is not particularly limited, but it is generally preferable to use particles that have a sphere shape, a plate shape, or a needle shape, in view of availability.

The amount of the metal or metal oxide (a) used is preferably 20 mass % or more and 70 mass % or less relative to the total mass of (a), (b), and (c), in view of ensuring the electron conductivity of the detection electrode and obtaining a high detecting performance for a target gas. In view of more markedly exhibiting these advantageous effects, the amount of the metal (a) used is more preferably 30 mass % or more and 60 mass % or less, and even more preferably 40 mass % or more and 55 mass % or less, relative to the total mass of (a), (b), and (c).

The cation conductive carbonate (b) is used to impart cation conductivity to the detection electrode. Examples of the cation include alkali metal ions such as lithium ions and sodium ions. From this viewpoint, the cation conductive carbonate is preferably an alkali metal salt of carbonic acid. For example, the cation conductive carbonate is preferably lithium carbonate ($Li_2CO_3$).

The amount of the cation conductive carbonate (b) used is preferably 5 mass % or more and 55 mass % or less relative to the total mass of (a), (b), and (c), in view of efficiently forming a three-phase interface in the detection electrode and accurately detecting carbonic acid gas in an atmosphere as an object of measurement. In view of more markedly exhibiting these advantageous effects, the amount of the cation conductive carbonate (b) used is more preferably 7 mass % or more and 50 mass % or less, and even more preferably 10 mass % or more and 40 mass % or less, relative to the total mass of (a), (b), and (c).

The lithium-containing oxide (c) is an oxide containing Li and at least one of Ce and Sm, and functions to assist the conduction of anions that migrate through the solid electrolyte layer and cations that migrate through the cation conductive carbonate. The lithium-containing oxide (c) may be a conductor for both ions. For example, in the case where the solid electrolyte layer and the cation conductive carbonate are oxide ion conductive and lithium ion conductive, respectively, the lithium-containing oxide (c) may have both oxide ion conductivity and lithium ion conductivity.

The material for the lithium-containing oxide (c) may be $Li_2LnO_3$, where Ln represents at least one rare-earth element, $Li_2ZrO_3$, or $Li_6Zr_3O_7$, for example. Examples of $Li_2LnO_3$ include $Li_2CeO_3$, and $Li_2Ce_xSm_yO_3$, where x and y represent positive numbers, and x+v=1. Also, a mixture of a lithium oxide and an oxide containing at least one of Zr, Ce, and Sm may be used. These materials are preferably used in the form of particles.

The amount of the lithium-containing oxide (c) used is preferably 10 mass % or more and 60 mass % or less relative to the total mass of (a), (b), and (c), in view of efficiently forming a three-phase interface in the detection electrode and accurately detecting carbonic acid gas in an atmosphere as an object of measurement. In view of more markedly exhibiting these advantageous effects, the amount of the lithium-containing oxide (c) used is more preferably 20 mass % or more and 50 mass % or less, and even more preferably 30 mass % or more and 40 mass % or less, relative to the total mass of (a), (b), and (c).

Preferably, the above described components (a), (b), and (c) are uniform in the mixture of (a), (b), and (c). Such a uniform mixture leads to the increase in the contact area between (a), (b), and (c) and the decrease in the interface resistance, which facilitates the operation of the carbon dioxide sensor according to the present invention at a lower temperature. In addition, since the components (a), (b), and (c) are mixed with each other, the electromotive force is unlikely to depend on the thickness of the detection electrode, and therefore, advantageously, the electromotive force is unlikely to vary between sensors.

From the same viewpoint, it is preferable that the components (a) and (c) be continuously formed in the mixture. The expression "the contact structure of the components (a) and (c) is continuously formed" means a state in which the particles of (a) and the particles of (c) are in contact with each other to continuously form a conductive path through which electrons and both ions flow. Whether or not the contact structure of (a) and (c) is formed can be determined by observing a surface and/or a cross section of the mixture using a scanning electron microscope (SEM) at a magnification of, for example, 100× to 10000×, and optionally performing elemental mapping using an energy dispersive X-ray spectroscopy (EDS).

In contrast thereto, in conventional carbon dioxide sensors, such as the carbon dioxide sensors disclosed in JP 2008-267845A and Sensors and Actuators B24-25 (1995) 260-265, the components (a), (b), and (c) are in the form of separate and independent layers, and only the surfaces of the layers are in contact with each other. Accordingly, there is a limitation in increasing the contact area, and as a result, it is difficult to lower the operating temperature.

The detection electrode is formed preferably by mixing the components (a), (b), and (c) at a predetermined mixing ratio, adding an organic solvent to the mixture to obtain a paste, applying the paste to the surface of the solid electrolyte layer or the surface of an intermediate layer, which will be described later, to form a coating film, and calcining the coating film. The calcination temperature can be preferably 400° C. or more and 1400° C. or less, more preferably 500° C. or more and 1200° C. or less, and even more preferably 600° C. or more and 1000° C. or less. The calcination time is preferably 0.1 hours or more and 20 hours or less, more preferably 0.5 hours or more and 15 hours or less, and even more preferably 1 hour or more and 10 hours or less.

In the preparation of the paste, the amount of the component (a) is preferably 20 mass % or more and 70 mass % or less, more preferably 30 mass % or more and 60 mass % or less, and even more preferably 40 mass % or more and 55 mass % or less, relative to the total amount of (a), (b), and (c).

The amount of the component (b) is preferably 5 mass % or more and 55 mass % or less, more preferably 7 mass % or more and 40 mass % or less, and even more preferably 10 mass % or more and 30 mass % or less, relative to the total amount of (a), (b), and (c).

The amount of the component (c) is preferably 10 mass % or more and 60 mass % or less, more preferably 15 mass % or more and 50 mass % or less, and even more preferably 20 mass % or more and 40 mass % or less, relative to the total amount of (a), (b), and (c).

The carbon dioxide sensor according to the present invention may include at least one of an intermediate layer between the solid electrolyte layer and the reference electrode and an intermediate layer between the solid electrolyte layer and the detection electrode. The intermediate layer is used for the purpose of improving the anion conductivity, for example, the oxide ion conductivity between the solid electrolyte layer and the reference electrode and/or the detection electrode. For reducing the electric resistance in the carbon dioxide sensor, it is important to enhance the anion conductivity of the solid electrolyte layer. However, even if a solid electrolyte layer made of a material with high anion conductivity is used, there is a limitation in enhancing the anion conductivity in the carbon dioxide sensor as a whole when the anion conductivity between the solid electrolyte layer and the reference electrode and/or the detection electrode is low. As a result of studies, the inventors of the present invention have found that the anion conductivity of the carbon dioxide sensor as a whole can be increased by disposing an intermediate layer made of a specific material between the solid electrolyte layer and the reference electrode and/or that between the solid electrolyte layer and the detection electrode. Specifically, it has been found that, when the intermediate layer is made of cerium oxide doped with lanthanum and a rare-earth element, provided that lanthanum and cerium are excluded from the rare-earth element (hereinafter also referred to as "La-LnDC"), the anion conductivity, in particular, the oxide ion conductivity of the carbon dioxide sensor is enhanced.

For the La-LnDC for the intermediate layer, examples of the rare-earth element doped into the cerium oxide include samarium, gadolinium, yttrium, erbium, ytterbium, and dysprosium. These rare-earth elements may be used singly or in a combination of two or more. In particular, the intermediate layer preferably contains cerium oxide doped with lanthanum and samarium or gadolinium in view of further enhancing the anion conductivity, in particular, the oxide ion conductivity of the carbon dioxide sensor as a whole. The material of the intermediate layer disposed between the reference electrode and the solid electrolyte layer (hereinafter also referred to as "reference electrode-side intermediate layer") may be the same as or different from the material of the intermediate layer disposed between the detection electrode and the solid electrolyte layer (hereinafter also referred to as "detection electrode-side intermediate layer"). One of the reference electrode-side intermediate layer and the detection electrode-side intermediate layer may contain a La-LnDC while the other intermediate layer contains a different substance.

In the intermediate layer, the ratio of the rare-earth element other than lanthanum doped into the cerium oxide, and specifically, the atomic ratio of the rare-earth element (Ln) to cerium, Ln/Ce, is preferably 0.05 or more and 0.8 or less, more preferably 0.1 or more and 0.7 or less, and even more preferably 0.2 or more and 0.6 or less. The rare-earth element doped in an amount within the above-described range improves the anion conductivity, in particular, the oxide ion conductivity between the solid electrolyte layer and the reference electrode and/or the detection electrode.

The value of Ln/Ce is measured using energy-dispersive X-ray spectroscopy (hereinafter also referred to as "EDS"), an electron probe micro analyzer (hereinafter also referred to as "EPMA"), or the like.

The La-LnDC for the intermediate layer contains lanthanum for the purpose of improving the anion conductivity, in particular, the oxide ion conductivity of the carbon dioxide sensor as a whole. For this purpose, the atomic ratio of lanthanum to cerium, La/Ce, in the intermediate layer is preferably 0.08 or more. When the amount of lanthanum is too large, the anion conductivity decreases, and accordingly, the ratio La/Ce is preferably 1.2 or less. The ratio La/Ce is more preferably 0.2 or more and 1.2 or less, and even more preferably 0.3 or more and 1.2 or less. The ratio La/Ce is measured using EDS, EPMA, or the like.

When the intermediate layer has a thickness greater than or equal to a certain value, the anion conductivity, in particular, the oxide ion conductivity between the solid electrolyte layer and the reference electrode and/or the detection electrode can be effectively improved. More specifically, the reference electrode-side intermediate layer and the detection electrode-side intermediate layer each independently have a thickness of preferably 0.1 μm or more and 1.0 μm or less, and more preferably 0.3 μm or more and 0.8 μm or less. The thickness of the intermediate layer can be measured by observing a cross section using a stylus profilometer or an electron microscope. The thickness of the reference electrode-side intermediate layer and the thickness of the detection electrode-side intermediate layer may be the same or different.

As described hereinabove, the solid electrolyte layer included in the carbon dioxide sensor according to the present invention is anion conductive. For example, in the case where the solid electrolyte layer is oxide ion conductive, the solid electrolyte layer preferably contains an oxide of lanthanum. Examples of the oxide ion conductive material containing an oxide of lanthanum include: composite oxides containing lanthanum and gallium optionally doped with, for example, strontium, magnesium, or cobalt; and composite oxides containing lanthanum and molybdenum. In particular, it is preferable to use a composite oxide containing lanthanum and silicon because of its high oxide ion conductivity.

The composite oxide containing lanthanum and silicon may be, for example, a composite oxide having an apatite crystal structure and containing lanthanum and silicon. In view of high oxide ion conductivity, it is preferable to use, as the composite oxide having an apatite crystal structure, a composite oxide that contains lanthanum, which is a trivalent element, silicon, which is a tetravalent element, and O, and has a composition represented by $La_xSi_6O_{1.5x+12}$, wherein X represents a number of 8 or more and 10 or less. The most preferable composition of the composite oxide having an apatite crystal structure is $La_{9.33}Si_6O_{26}$. The composite oxide having an apatite crystal structure can be produced according to, for example, the method disclosed in JP 2013-51101A.

Another preferable example of the solid electrolyte layer is a compound containing $M^1$, $M^2$, and O. This compound can further enhance the oxide ion conductivity of the solid electrolyte layer. $M^1$ represents one or more elements selected from the group consisting of La, Ce, Pr, Nd, Pm, Sm, Eu, Gd, Tb, Dy, Ho, Er, Yb, Lu, Be, Mg, Ca, Sr, Y, and Ba. $M^2$ represents one or more elements selected from the group consisting of Mg, Al, Sc, Ti, V, Cr, Mn, Fe, Co, Ni, Ga, Zr, Ta, Nb, B, Si, Ge, Zn, Sn, W, and Mo. The compound preferably has an apatite crystal structure.

In particular, it is preferable that the solid electrolyte layer be a composite oxide represented by formula (1): $M^1_{9.33+x}$ $[T_{6.00-y}M^2_y]O_{26.0+z}$, in view of further enhancing the oxide ion conductivity of the solid electrolyte layer. In the formula. $M^1$ represents one or more elements selected from the group consisting of La, Ce, Pr, Nd, Pm, Sm, Eu, Gd, Tb, Dy, Ho, Er, Yb, Lu, Be, Mg, Ca, Sr, Y, and Ba. T represents either one or both of Si and Ge. $M^2$ represents one or more elements selected from the group consisting of Mg, Al, Sc, Ti, V, Cr, Mn, Fe, Co, Ni, Ga, Zr, Ta, Nb, B, Si, Ge, Zn, Sn, W, and Mo. x represents a number of −1.33 or more and 1.50 or less. y represents a number of 0.00 or more and 3.00 or less. z represents a number of −5.00 or more and 5.20 or less. The ratio of the number of moles of $M^1$ to the number of moles of T is 1.33 or more and 3.61 or less. The composite oxide preferably has an apatite crystal structure.

Among the elements listed above for $M^1$ in the formula (1), La, Ce, Pr, Nd, Sm, Eu, Gd, Tb, Dy, Be, Mg, Ca, Sr, Y, and Ba, have the following common features: they are lanthanoids or Group II metals that may turn into ions with positive charges and be incorporated into an apatite hexagonal crystal structure. Among these, $M^1$ preferably represents one or more elements selected from the group consisting of La, Nd, Ba, Sr, Ca, Y, and Ce, in view of further enhancing the oxide ion conductivity. In particular. $M^1$ preferably contains at least La and Y. In the formula (1), T preferably contains either one or both of Si and Ge.

In the formula (1), the element represented by $M^2$ is preferably one or more elements selected from the group consisting of B, Zn, W, Sn, and Mo, for example. Among these, B, Zn, and W are particularly preferable in view of high degree of orientation and high productivity.

In view of increasing the degree of orientation and the oxide ion conductivity, x in the formula (1) preferably represents a number of −1.33 or more and 1.50 or less, more preferably −1.00 or more and 1.00 or less, and even more preferably 0.00 or more and 0.70 or less. In particular, x preferably represents 0.45 or more and 0.65 or less. In view of filling the position of the element represented by T in the apatite crystal lattice and enhancing the oxide ion conductivity, y in the formula (1) preferably represents a number of 0.00 or more and 3.00 or less, more preferably 0.40 or more and less than 1.00, and even more preferably 0.40 or more and 0.90 or less. Furthermore, y especially preferably represents 0.80 or less, in particular, 0.70 or less, and more particularly 0.50 or more and 0.70 or less. In view of maintaining the electrical neutrality in the apatite crystal lattice, z in the formula (1) preferably represents a number of −5.00 or more and 5.20 or less, more preferably −3.00 or more and 2.00 or less, and even more preferably −2.00 or more and 1.50 or less. In particular, z preferably represents a number of −1.00 or more and 1.00 or less.

In the formula (1), the ratio of the number of moles of $M^1$ to the number of moles of T, or in other words, (9.33+x)/ (6.00−y) is preferably 1.33 or more and 3.61 or less, more preferably 1.40 or more and 3.0) or less, and even more preferably 1.50 or more and 2.50 or less, in view of maintaining the spatial occupation in the apatite crystal lattice.

The composite oxide represented by the formula (1) can be produced according to, for example, the method disclosed in WO 2016/111110.

The thickness of the solid electrolyte layer is preferably 1 μm or more and 1000 μm or less, more preferably 10 μm or more and 500 μm or less, and even more preferably 100 μm or more and 500 μm or less, in view of maintaining strength of the carbon dioxide sensor and effectively reducing the electric resistance between the reference electrode and the detection electrode. The thickness of the solid electrolyte layer can be measured by observing a cross section using a stylus profilometer or an electron microscope.

The reference electrode used in the carbon dioxide sensor according to the present invention can be made by using, for example, a metal material. The metal material preferably contains a platinum group element because the catalytic activity for the reactions of oxygen absorption and desorption is necessary. Examples of the platinum group element include platinum, ruthenium, rhodium, palladium, osmium, and iridium. These elements may be used singly or in a combination of two or more. A cermet that contains a platinum group element can also be used in the reference electrode.

When the carbon dioxide sensor according to the present invention is placed in a gas phase that contains carbon dioxide (for example, in the air, or in the exhaust gas of an internal combustion engine), a reaction (see formula (A) given below) takes place according to the carbon dioxide concentration at a three-phase interface where the gas phase and the electrode are in contact to reach an equilibrium state. On the other hand, on the reference electrode side, a reaction represented by the following formula (B) proceeds in response to the reaction represented by formula (A). Accordingly, it is advantageous that the detection electrode and the reference electrode have a large contact area with the gas phase, and thus the detection electrode and the reference electrode are preferably porous. Furthermore, in the detection electrode, a structure is more preferably formed continuously in which a metal that continuously conduct electrons in the depth direction and the lithium-containing oxide are in contact, to thereby form a path that conducts electrons and both ions.

Due to the above-described mechanism, an electromotive force is generated between the detection electrode and the reference electrode. The electromotive force varies according to the carbon dioxide concentration in the gas phase. Thus, by using the electromotive force, carbon dioxide can be detected, and the carbon dioxide concentration can be measured.

As described above, the detection electrode in the carbon dioxide sensor according to the present invention contains a mixture of the components (a), (b), and (c), and it is therefore possible to improve the detection performance of the carbon dioxide sensor as compared with a conventional carbon dioxide sensor. In particular, it is considered that, by including the component (c), an ionically conductive path that conduct both lithium ions and oxide ions can be formed, and that the reaction represented by the following formula (A) is thus likely to proceed. The electrochemical reaction that takes place in the detection electrode of the carbon dioxide sensor according to the present invention is represented by the following formula (A), and thus as long as the carbon dioxide sensor operates normally, the number of reaction electrons is 2. Accordingly, the number of reaction electrons in the detection electrode while the carbon dioxide sensor is operating is determined, and if the number of reaction electrons is 2 or a number close to 2, it can be determined that the carbon dioxide sensor is operating normally. For example, the number of reaction electrons is preferably 2.0±1.0 when the carbon dioxide sensor according to the present invention is operated at 500° C., and the number of reaction electrons is preferably 2.0±0.2 when the carbon dioxide sensor according to the present invention is operated at 400° C. If the number of reaction electrons significantly deviates from 2, it means that an unintended reaction other than the reactions represented by the following formulas (A) and (B) are occurring, the unintended reaction being independent of the carbon dioxide concentration.

[Chem. 1]

$$2Li^+ + CO_2 + (\tfrac{1}{2})O_2 + 2e^- \leftrightarrows Li_2CO_3 \qquad (A)$$

$$(\tfrac{1}{2})O_2 + 2e^- \leftrightarrows O^{2-} \qquad (B)$$

In view of improving the detection performance, the thickness of the detection electrode is preferably 5 μm or more and 2000 μm or less, more preferably 10 μm or more and 1000 μm or less, and even more preferably 20 μm or more and 500 μm or less. The thickness of the detection electrode can be measured by observing a cross section with a stylus profilometer or an electron microscope.

EXAMPLES

Hereinafter, the present invention will be described in further detail by way of examples. However, the scope of the present invention is not limited to the examples given below. Unless otherwise stated, the percent sign "%" used herein means "mass %".

Example 1

A carbon dioxide sensor was produced by performing the following steps (1) to (4).
(1) Production of Solid Electrolyte Layer $La_2O_3$ powder and $SiO_2$ powder were blended at a molar ratio of 1:1, ethanol was added thereto, and they were mixed using a ball mill. The mixture was dried, pulverized using a motor, and calcined using a platinum crucible at 1650° C. in an air atmosphere for three hours. Ethanol was added to the calcined product, and the resulting mixture was pulverized using a planetary ball mill to obtain a calcined powder. The calcined powder was placed in a 20-mmφ compression mold, and uniaxially compressed by pressing in one direction. Furthermore, cold isostatic pressing (CIP) was performed at 600 MPa for one minute to thereby obtain a pellet. The obtained pellet was heated at 1600° C. in the air for three hours to thereby obtain a calcined pellet. The calcined pellet was subjected to powder X-ray diffractometry and chemical analysis, and as a result, it was found that the calcined pellet had a structure of $La_2SiO_5$.

800 mg of the obtained pellet and 140 mg of $B_2O_3$ powder were placed in a saggar with a lid, and heated at 1550° C. (furnace atmospheric temperature) in the air for 50 hours using an electric furnace. As a result of heating. $B_2O_3$ vapor was generated in the saggar, and the $B_2O_3$ vapor reacted with the pellet, to thereby obtain an intended solid electrolyte layer. The solid electrolyte layer had an apatite crystal structure and had the following compositional formula: $La_{9.33+x}[Si_{6.00-y}B_y]O_{26.0+z}$, where x=0.50, y=1.17, and z=0.16. The molar ratio of La to Si was 2.04. Hereinafter, this compound will be referred to simply as "LSBO". The oxide ion conductivity at 500° C. was $3.0 \times 10^{-2}$ S/cm. The thickness of the solid electrolyte layer was 350 μm.
(2) Formation of Intermediate Layer $Sm_{0.2}Ce_{1.8}O_2$ powder was placed in a 50-mmφ compression mold, and uniaxially compressed by pressing in one direction, followed by hot press sintering. As for the sintering conditions, the sintering was performed in a nitrogen gas atmosphere at a pressure of 30 MPa and a temperature of 1200° C. for three hours. In this way, a sputtering target was obtained. Using the obtained target, radio frequency sputtering was performed on each surface of the solid electrolyte layer to form a sputtering layer made of samarium-doped cerium oxide (hereinafter also referred to as "SDC"). As for the sputtering conditions, the sputtering was performed at an RF output of 30 W and an argon gas pressure of 0.8 Pa. After the sputtering, annealing was performed at 1500° C. in the air for one hour to thermally diffuse the lanthanum contained in the solid electrolyte layer into the sputtering layer to thereby incorporate lanthanum into the SDC. In this way, a reference electrode-side intermediate layer and a detection electrode-side intermediate layer, each containing lanthanum-containing SDC (hereinafter also referred to as "La-SDC"), were formed. The value of La/Ce of the reference electrode-side intermediate layer and the detection electrode-side intermediate layer measured using EDS was 0.98.
(3) Formation of Reference Electrode A platinum powder-containing paste was applied to the surface of the reference electrode-side intermediate layer to form a coating film. The coating film was calcined at 700° C. in the air for one hour to form a reference electrode in the form of a porous body.
(4) Formation of Detection Electrode As the metal (a), the cation conductive carbonate (b), and the lithium-containing oxide (c), those listed in Table 1 given below were used. The metal (a) had a particle size $D_{50}$ of 1.0 μm. A paste was prepared by mixing them at a ratio shown in Table 1 and adding ethanol thereto. The paste was applied to the surface of the detection electrode-side intermediate layer to form a coating film. The coating film was calcined at 700° C. in carbon dioxide gas for ten hours to obtain a detection electrode. A cross section of the detection electrode was observed under SEM at a magnification of 2000× and subjected to elemental mapping by EDS, and as a result, it was found that the components (a) and (c) were continuously formed. The thickness of the detection electrode was 20 μm.

Examples 2 to 4

A carbon dioxide sensor was produced in the same manner as Example 1, except that, as the metal (a), the cation conductive carbonate (b), and the lithium-containing oxide (c), those listed in Table 1 given below were used at the ratio shown in Table 1. The detection electrode of each sensor of Examples 2 to 4 was observed in the same manner as in Example 1, and as a result, it was found that the components (a) and (c) were formed continuously. The thickness of the detection electrode was 20 μm.

Examples 5 to 8

A carbon dioxide sensor was produced in the same manner as Example 1, except that, in the production of the solid-state electrolyte, $Y_2O_3$ powder, $La_2O_3$ powder, and $SiO_2$ powder were blended at a molar ratio of 0.2:0.8:1.0, and that as the metal (a), the cation conductive carbonate (b), and the lithium-containing oxide (c), those listed in Table 1 given below were used at the ratio shown in Table 1. The resulting solid electrolyte layer in the carbon dioxide sensor had an apatite crystal structure and the following compositional formula: $La_{8.0}Y_{1.7}Si_{5.3}B_{0.7}O_{26.7}$. This compositional formula thus corresponds to $M^1_{9.33+x}[T_{6.00-y}M^2_y]O_{26.0+z}$, wherein x=0.37, y=0.70, z=0.70, and the molar ratio of the total of La and Y to Si was 1.83 (hereinafter, this compound will be referred to simply as "Y-LSBO"). The oxide ion conductivity at 500° C. was 0.9×10⁻³ S/cm. The thickness of the solid electrolyte layer was 350 μm.

Comparative Example 1

In this comparative example, the lithium-containing oxide (c) was not used in the production of the detection electrode, and more specifically, as the metal (a) and the cation conductive carbonate (b), those listed in Table 1 given below were used at the ratio shown in Table 1. A carbon dioxide sensor was produced in the same manner as Example 1, except for the above.

Comparative Example 2

A carbon dioxide sensor was produced in the same manner as in Example 5 except that as the metal (a) and the cation conductive carbonate (b), those listed in Table 1 given below were used at the ratio shown in Table 1 without the lithium-containing oxide (c).
Evaluation The carbon dioxide sensors obtained in Examples and Comparative Examples were operated at 400° C. and 500° C. in the air, and the number of reaction electrons in the detection electrode during the operation was measured using the following method. If the carbon dioxide sensor operates normally, the number of reaction electrons, n, is theoretically 2.
Measurement of Number of Reaction Electrons The number of reaction electrons can be calculated using Nernst equation, i.e., the following formula (C). R represents a gas constant, T represents an absolute temperature, F represents a Faraday constant, and $P(CO_2)$ represents the partial pressure of $CO_2$.

$$E=E^0+(RT/nF)\ln P(CO_2) \tag{C}$$

2. In contrast, in the carbon dioxide sensor of Comparative Example 1, the number of reaction electrons was a value far from 2, which suggests that an unintended reaction independent of the carbon dioxide concentration occurred. In Table 1, a hyphen "-" indicates that measurement at 400° C. was not performed, and thus no numerical value is shown.

The above results mean that the carbon dioxide sensors of Examples are appropriate for measuring the carbon dioxide concentration at a temperature lower than or equal to 600° C.

INDUSTRIAL APPLICABILITY

The present invention provides a carbon dioxide sensor that can operate at a temperature lower than the operating temperatures of conventional carbon dioxide sensors, and the carbon dioxide sensors according to the present invention are unlikely to vary in the electromotive forces. Also, an appropriate method for measuring the carbon dioxide concentration at a temperature lower than or equal to 600° C. is provided.

The invention claimed is:
1. A carbon dioxide sensor comprising:
   a solid electrolyte layer that is anion conductive;
   a reference electrode disposed on one surface of the solid electrolyte layer; and
   a detection electrode disposed on an opposite surface of the solid electrolyte layer,
   wherein the detection electrode is made of a mixture containing:
       particles of one or more metals selected from the group consisting of Au, Ag, Pt, Pd, Rh, Ru, Os, and Ir;
       a cation conductive carbonate; and
       particles of an oxide comprising $Li_2Ce_xSm_yO_3$ where x and y represent positive numbers, and x+y=1,

TABLE 1

| | Solid electrolyte | (a) Metal (mass %) | (b) Cation conductive carbonate (mass %) | (c) Lithium-containing oxide (mass %) | Number of reaction electrons 400° C. | Number of reaction electrons 500° C. |
|---|---|---|---|---|---|---|
| Example 1 | LSBO | Au (45.2) | Li₂CO₃ (22.6) | LiCeO₃ (32.2) | 2.17 | 2 37 |
| Example 2 | LSBO | Au (44.4) | Li₂CO₃ (23.8) | LiCeO₃ (31.8) | 2.17 | 1.55 |
| Example 3 | LSBO | Au (50.0) | Li₂CO₃ (14.3) | LiCeO₃ (35.7) | — | 1.85 |
| Example 4 | LSBO | Au (51.9) | Li₂CO₃ (11.1) | LiSm₀.₂Ce₀.₈O₂ (37.0) | — | 3.00 |
| Example 5 | Y-LSBO | Au (45.2) | Li₂CO₃ (22.6) | LiCeO₃ (32.3) | 2.20 | 1.60 |
| Example 6 | Y-LSBO | Au (43.8) | Li₂CO₃ (25.0) | LiCeO₃ (31.3) | 2.00 | 1.90 |
| Example 7 | Y-LSBO | Au (51-9) | Li₂CO₃ (11.1) | LiCeO₃ (37.0) | — | 2.81 |
| Example 8 | Y-LSBO | Au (46.7) | Li₂CO₃ (20.0) | LiSm₀.₂Ce₀.₈O₂ (33.3) | 2.75 | 2.73 |
| Comparative Example 1 | LSBO | Au (50.0) | Li₂CO₃ (50.0) | Not used | — | 5.64 |
| Comparative Example 2 | Y-LSBO | Au (50.0) | Li₂CO₃ (50.0) | Not used | — | 3.85 |

As is clear from the results shown in Table 1, in the carbon dioxide sensors of Examples, the number of reaction electrons at an operating temperature of 500° C. was a value close to 2, and the number of reaction electrons at an operating temperature of 400° C. was a value much closer to wherein the one or more metals are contained in an amount that ranges between 30 mass % or more and 60 mass % or less relative to a total mass of the one or more metals, the cation conductive carbonate, and the oxide, and wherein a contact structure of the particles of the one or more metals and the particles of the oxide is continuously formed in the mixture.

2. The carbon dioxide sensor according to claim 1, wherein, in the mixture, the amount of the cation conductive carbonate is 5 mass % or more and 55 mass % or less relative to the total mass of the one or more metals, the cation conductive carbonate, and the oxide.

3. The carbon dioxide sensor according to claim 1, wherein, in the mixture, the amount of the oxide is 10 mass % or more and 60 mass % or less relative to the total mass of the one or more metals, the cation conductive carbonate, and the oxide.

4. The carbon dioxide sensor according to claim 1, further comprising a first intermediate layer between the solid electrolyte layer and the reference electrode, the first intermediate layer being made of cerium oxide doped with lanthanum and a rare-earth element, provided that lanthanum and cerium are excluded from the rare-earth element.

5. The carbon dioxide sensor according to claim 1, wherein the solid electrolyte layer is oxide ion conductive.

6. The carbon dioxide sensor according to claim 1, wherein the solid electrolyte layer is made of a compound containing $M^1$, $M^2$, and O, where $M^1$ represents one or more elements selected from the group consisting of La, Ce, Pr, Nd, Pm, Sm, Eu, Gd, Tb, Dy, Ho, Er, Yb, Lu, Be, Mg, Ca, Sr, Y, and Ba, and $M^2$ represents one or more elements selected from the group consisting of Mg, Al, Sc, Ti, V, Cr, Mn, Fe, Co, Ni, Ga, Zr, Ta, Nb, B, Si, Ge, Zn, Sn, W, and Mo.

7. The carbon dioxide sensor according to claim 6, wherein $M^1$ includes at least La and Y.

8. The carbon dioxide sensor according to claim 1, wherein the solid electrolyte layer is made of a composite oxide represented by formula (1): $M_{9.33+x}^{1}[T_{6.00-y}M_{y}^{2}]O_{26.0+z}$, where $M^1$ represents one or more elements selected from the group consisting of La, Ce, Pr, Nd, Pm, Sm, Eu, Gd, Tb, Dy, Ho, Er, Yb, Lu, Be, Mg, Ca, Sr, Y, and Ba, T represents either one or both of Si and Ge, $M^2$ represents one or more elements selected from the group consisting of Mg, Al, Sc, Ti, V, Cr, Mn, Fe, Co, Ni, Ga, Zr, Ta, Nb, B, Si, Ge, Zn, Sn, W, and Mo, x represents a number of −1.33 or more and 1.50 or less, y represents a number of 0.00 or more and 3.00 or less, z represents a number of −5.00 or more and 5.20 or less, and the ratio of the number of moles of $M^1$ to the number of moles of T is 1.33 or more and 3.61 or less.

9. The carbon dioxide sensor according to claim 1, wherein the solid electrolyte layer is made of a compound having an apatite crystal structure.

10. The carbon dioxide sensor according to claim 1, wherein the solid electrolyte layer has a thickness of 1 μm or more and 1000 μm or less.

11. The carbon dioxide sensor according to claim 1, wherein the detection electrode has a thickness of 5 μm or more and 2000 μm or less.

12. The carbon dioxide sensor according to claim 1, further comprising a second intermediate layer between the solid electrolyte layer and the detection electrode, the second intermediate layer being made of cerium oxide doped with lanthanum and a rare-earth element, provided that lanthanum and cerium are excluded from the rare-earth element.

13. The carbon dioxide sensor according to claim 1, wherein the cation conductive carbonate is contained in an amount that ranges between 7 mass % or more and 30 mass % or less relative to the total mass of the one or more metals, the cation conductive carbonate, and the oxide.

14. The carbon dioxide sensor according to claim 1, wherein the oxide is contained in an amount that ranges between 20 mass % or more and 40 mass % or less relative to total mass of the one or more metals, the cation conductive carbonate, and the oxide.

15. The carbon dioxide sensor according to claim 1, wherein the one or more metals have a particle size of 0.05 μm or more and 5 μm or less.

16. A method for measuring a carbon dioxide concentration, the method comprising using the carbon dioxide sensor according to claim 1 at a temperature lower than or equal to 600° C.

* * * * *